(12) United States Patent
Pawar et al.

(10) Patent No.: US 8,795,441 B2
(45) Date of Patent: Aug. 5, 2014

(54) REWORKING OF SURFACE OXIDIZED AND NITRIDED COMPONENTS

(75) Inventors: Vivek Pawar, Germantown, TN (US); Shilesh C. Jani, Germantown, TN (US); Carolyn Weaver, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1271 days.

(21) Appl. No.: 11/740,006

(22) Filed: Apr. 25, 2007

(65) Prior Publication Data

US 2007/0251604 A1    Nov. 1, 2007

Related U.S. Application Data

(60) Provisional application No. 60/795,102, filed on Apr. 26, 2006.

(51) Int. Cl.
*C23C 8/80* (2006.01)
*C22C 16/00* (2006.01)

(52) U.S. Cl.
USPC .................................. 148/208; 148/421

(58) Field of Classification Search
USPC ............................................... 148/208, 421
See application file for complete search history.

(56) References Cited

U.S. PATENT DOCUMENTS

| | | | |
|---|---|---|---|
| 2,987,352 A | | 6/1961 | Watson |
| 3,287,111 A | * | 11/1966 | Klepfer ..................... 420/422 |
| 3,615,885 A | | 10/1971 | Watson et al. |
| 4,160,680 A | * | 7/1979 | Novy et al. ................. 148/218 |
| 4,238,251 A | * | 12/1980 | Williams et al. ............ 148/672 |
| 4,860,757 A | * | 8/1989 | Lynch et al. ................ 600/434 |
| 5,037,438 A | | 8/1991 | Davidson |
| 5,152,794 A | | 10/1992 | Davidson |
| 5,180,394 A | | 1/1993 | Davidson |
| 5,372,660 A | * | 12/1994 | Davidson et al. ........... 148/421 |
| 5,399,207 A | | 3/1995 | Kemp |
| 5,840,610 A | * | 11/1998 | Gilmer et al. ............... 438/301 |
| 6,059,830 A | | 5/2000 | Lippincott, III et al. |
| 6,447,550 B1 | | 9/2002 | Hunter et al. |
| 6,585,772 B2 | | 7/2003 | Hunter et al. |
| 6,726,725 B2 | | 4/2004 | Hunter et al. |
| 6,833,197 B1 | | 12/2004 | Dong et al. |
| 6,881,229 B2 | | 4/2005 | Khandkar et al. |
| 7,048,767 B2 | | 5/2006 | Namavar |
| 7,070,623 B2 | | 7/2006 | Hunter et al. |
| 2005/0033442 A1 | | 2/2005 | Fisher et al. |
| 2006/0169364 A1 | * | 8/2006 | Trotzschel et al. .......... 148/269 |

FOREIGN PATENT DOCUMENTS

| | | | |
|---|---|---|---|
| EP | 0 410 711 | 1/1991 | |
| EP | 0 608 997 | 8/1994 | |
| JP | 07-173587 | * 7/1995 | |
| WO | WO 99/04055 | 1/1999 | |
| WO | WO 2005/037468 | * 4/2005 | ............... B22F 3/24 |

OTHER PUBLICATIONS

Cox, B., "A mechanism for the hydrogen uptake process in zirconium alloys", Journal of Nuclear Materials, 264 (1999) pp. 283-294.*
J.D. Ehrman et al., "Micrrobial adhesion to zirconium alloys", Colloids and Surfaces B: Biointerfaces, 50 (2006) pp. 152-159.*
Easterday, C.L., Ashtabula, Ohio, "Zirconium Analysis by Production Control Quantometer" Analytical Chemistry (U.S.) Formerly Ind. Eng. Chem., Anal. Ed.; vol. 31, No. 11, pp. 1867-1868, Nov. 1, 1959.*
D.M. Brunette, P. Tengvall, M. Textor, and P. Thomsen, "Titanium in Medicine, "Properties and Biological Significance of Natural Oxide Films on Titanium and Its Alloys, (Springer, Berlin, Germany, 2001), pp. 172-174 and 177.*
Hobbs et al., "Oxidation Microstructures and Interfaces in the Oxidized Zirconium Knee", *International Journal of Applied Ceramic Technology*, 2005, 221-246, vol. 2 (3).
Long et al., "Nano-Hardness Measurements of Oxidized Zr-2.5Nb and Various Orthopaedic Materials", *24th Annual Meeting of the Society for Biomaterials*, Apr. 22-26, 1998, San Diego, California, USA.
Sprague et al., "Mechanical Behavior of Zirconia, Alumina, and Oxidizen, Zirconium Modular Heads", *ISTA*, 2003, vol. 2.
Takamura, "Surface Hardening of Titanium by Oxygen", *Trans. JIM*, 1962, 10-14, vol. 3.
Treco, "Solution and Diffusion of Corrosion Oxide Film in Zircaloy", *J. Electrochem. Soc.*, 1962, 208-211, vol. 109.
R. Treco, J. Electrochem. Soc., vol. 109, p. 208, 1962.
Information Disclosure Statement by Applicant, U.S. Appl. No. 11/558,756, filed Jan. 30, 2007.
Supplemental Information Disclosure Statement by Applicant, U.S. Appl. No. 11/558,756, filed Dec. 18, 2007.
Second Supplemental Information Disclosure Statement by Applicant, U.S. Appl. No. 11/558,756, filed Aug. 29, 2008.
Revised Second Supplemental Information Disclosure Statement by Applicant, U.S. Appl. No. 11/558,756, filed Sep. 2, 2008.
Information Disclosure Statement by Applicant filed for U.S. Appl. No. 12/127,413 on May 27, 2008.
Information Disclosure Statement by Applicant filed for U.S. Appl. No. 12/244,492 on Jan. 23, 2009.
Information Disclosure Statement by Applicant filed for U.S. Appl. No. 12/244,492 on Aug. 9, 2010.

* cited by examiner

*Primary Examiner* — Jessee Roe
(74) *Attorney, Agent, or Firm* — Krieg DeVault LLP

(57) ABSTRACT

The present invention relates to a method of reworking a composition comprising a substrate and an oxidation and/or nitridation layer on the surface of the substrate by treating the composition under reduced pressure or in an inert gas environment at an elevated temperature until the oxidation and/or nitridation layer is substantially removed from the surface. In this way, manufacturing efficiencies and yields are improved as material that would otherwise have been scrapped is now used.

26 Claims, 2 Drawing Sheets

REWORKING OF SURFACE OXIDIZED AND NITRIDED COMPONENTS

CROSS-REFERENCE TO RELATED APPLICATIONS

This application claims priority to U.S. provisional application Ser. No. 60/795,102 filed Apr. 26, 2006. U.S. provisional application Ser. No. 60/795,102 filed Apr. 26, 2006 is incorporated by reference herein as though fully disclosed herein.

TECHNICAL FIELD

The present invention relates to a method of reworking surface oxidized and nitrided components to increase the efficiency of the manufacturing of such components by increasing manufacturing yields.

BACKGROUND OF THE INVENTION

Compositions comprising metallic substrates having deliberately (also referred to as pre-oxidized) oxidized or nitrided surfaces have many industrial, medical, and other applications. The use of such surfaces results in modified behavior of the interfacial surface regions to optimize their interaction with other materials. The manufacture of such compositions, like most manufacturing processes, typically results in yields of less than 100%. There is a need for improvement in the efficiency of the manufacture of such compositions, and this need is particularly acute where the cost of the substrate is high and the resulting costs of scrapping non-conforming material is high.

One field that has benefited from the use of compositions comprising metallic substrates having pre-oxidized or nitrided surfaces is the field of medical implants. Medical implant materials, in particular orthopedic implant materials, must combine high strength, corrosion resistance and tissue compatibility. The longevity of the implant is of prime importance especially if the recipient of the implant is relatively young because it is desirable that the implant function for the complete lifetime of a patient. Because certain metal alloys have the required mechanical strength and biocompatibility, they are ideal candidates for the fabrication of prostheses. These alloys include 316L stainless steel, chrome-cobalt-molybdenum alloys, titanium alloys and more recently zirconium alloys which have proven to be the most suitable materials for the fabrication of load-bearing prostheses.

To this end, oxidized zirconium orthopedic implants have been shown to reduce polyethylene wear significantly. The use of diffusion-hardened oxide surfaces such as oxidized zirconium in orthopedic applications was first demonstrated by Davidson in U.S. Pat. No. 5,037,438. Previous attempts have been made to produce oxidized zirconium layers on zirconium parts for the purpose of increasing their abrasion resistance. One such process is disclosed in U.S. Pat. No. 3,615,885 to Watson which discloses a procedure for developing thick (up to 0.23 mm) oxide layers on Zircaloy 2 and Zircaloy 4. However, this procedure results in significant dimensional changes especially for parts having a thickness below about 5 mm, and the oxide film produced does not exhibit especially high abrasion resistance.

U.S. Pat. No. 2,987,352 to Watson discloses a method of producing a blue-black oxide layer on zirconium alloy parts for the purpose of increasing their abrasion resistance. Both U.S. Pat. No. 2,987,352 and U.S. Pat. No. 3,615,885 produce a zirconium dioxide layer on zirconium alloy by means of air oxidation. U.S. Pat. No. 3,615,885 continues the air oxidation long enough to produce a beige layer of greater thickness than the blue-black layer of U.S. Pat. No. 2,987,352. This beige layer does not have the wear resistance of the blue-black layer and is thus not applicable to many parts where there are two work faces in close proximity. The beige layer wears down more quickly than the blue-black oxide layer with the resulting formation of oxidized zirconium particles and the loss of the integrity of the oxidized zirconium surface. With the loss of the oxide surface the zirconium metal is then exposed to its environment and can lead to transport of zirconium ions away from the surface of the metal into the adjacent environment.

The blue-black layers have a thickness which is less than that of the beige layer although the hardness of the blue-black layer is higher than that of the beige layer. This harder blue-black oxide layer lends itself better to surfaces such as prosthetic devices. Although the blue-black layer is more abrasion resistant than the beige layer it is a relatively thin layer. It is therefore desirable to produce the blue-black layers of increased abrasion resistance without producing the same type layers of the prior art.

As discussed above, U.S. Pat. No. 5,037,438 to Davidson discloses a method of producing zirconium alloy prostheses with a blue or blue-black oxidized zirconium surface. The prostheses of Davidson '438 exhibited exceptional wear characteristics. In U.S. Pat. No. 5,180,394, Davidson suggested the use of nitrided surfaces of zirconium or zirconium alloys. U.S. Pat. No. 2,987,352 to Watson discloses a method of producing zirconium bearings with a oxidized zirconium surface. The oxide layer produced is not always uniform in thickness and the non-uniformity reduces the integrity of the bonding between the zirconium alloy and the oxide layer and the integrity of the bonding within the oxide layer. Both U.S. Pat. No. 2,987,352 and U.S. Pat. No. 5,037,438 are incorporated by reference as though fully set forth herein.

In U.S. Pat. Nos. 6,447,550; 6,585,772 and pending U.S. application Ser. No. 10/942,464, Hunter, et al. described methods for obtaining an oxidized zirconium layer of uniform thickness. Hunter teaches that such is obtained by applying pre-oxidation treatment techniques and by manipulation of substrate microstructure. The use of uniform thickness oxide layer results in increased resistance to corrosion by the action of the body fluids as well as other benefits and is biocompatible and stable over the lifetime of the recipient. U.S. Pat. Nos. 6,447,550; 6,585,772 and pending U.S. application Ser. No. 10/942,464 are incorporated by reference as though fully set forth herein. In another approach of the prior art, Treco (R. Treco, J. Electrochem. Soc., Vol. 109, p. 208, 1962) used vacuum annealing method to dissolve the oxide formed on Zircalloy-2 after corrosion testing. The objective of Treco's work was to partially eliminate the oxide by vacuum annealing and then remove the hardened zone by acid pickling. Treco did not want to re-oxidize the samples hence the dissolution of oxide in the substrate and its influence on the re-oxidation was not considered.

The diffusion-hardened surfaces of Davidson and Hunter, while having relatively thick ceramic oxide or nitride layers, did not exhibit thick diffusion hardened zones below the ceramic oxide or nitride. The diffusion hardened zones of the compositions of Davidson and Hunter had thicknesses of at most 1-2 microns and typically less depending upon the conditions used to produce the composition. While the resulting compositions of Davidson and Hunter exhibited high wear resistance in comparison to those compositions available in the prior art, there is still room for improvement.

This significant reduction in wear in oxidized surfaces is attributed to its ceramic nature of the surface. The oxidized zirconium implant typically has 5 to 6 micron thick ceramic surface (zirconium oxide) that is formed by a thermally driven diffusion process in air. Beneath the zirconium oxide is a hard, oxygen-rich diffusion layer of approximately 1 to 2 micron. The totality of hardened zones (oxide plus diffusion hardened alloy) render the implant resistant to microscopic abrasion (third bodies such as bone cement, bone chips, metal debris, etc.) and slightly less resistant to macroscopic impact (surgical instrumentation and from dislocation/subluxation contact with metallic acetabular shells). The relatively small thickness of the hardened zones in the prior art oxidized zirconium compositions make them susceptible to damage caused by dislocation and subluxation. Thus, while the application of diffusion-hardened oxide layers such as oxidized zirconium to orthopedic implants has resulted in improvements in abrasion resistance and service life, there is room for improvement.

While the benefits to the use of oxidized zirconium, as well as other oxidized or nitrided compositions, are now well-known, improvements in the manufacture of such products are needed. One of the drawbacks of such products is that after oxidation or nitridation, if the parts do not meet specification, they are scrapped. The rework requires removal of the oxide by mechanical or chemical machining/polishing. Mechanical machining can lead to oxide particles embedment that can interfere with re-oxidation and/or re-nitridation. The re-work refers to a method or process applied on a part that does not meet the specification. The re-work dissolves or eliminates the oxide/nitride of the oxidized/nitrided surface. After rework, the components can be re-oxidized or re-nitrided (i.e., the oxide and/or nitride layers may be reformed after removal of the original oxidation and/or nitridation layers in the rework procedure). The removal of oxide by chemical means can alter the substrate surface and hence the re-oxidation characteristics. These rework techniques further more result in dimensional changes of the components. The inventors herein describe a process to rework oxidized or nitrided compositions to improve yield and manufacturing efficiency, thereby lowering the cost of products comprising oxidized or nitrided compositions, including medical implants comprising oxidized zirconium.

All of the above-referenced U.S. patents and published U.S. patent applications are incorporated by reference as though fully described herein.

BRIEF SUMMARY OF THE INVENTION

In one aspect of the present invention, there is a method of reworking a composition comprising a substrate and an oxidation and/or nitridation layer on the surface of the substrate, said method comprising the step of treating said composition under vacuum or reduced pressure or in an inert gas (such as argon) environment at a temperature of 500° C. or greater until said oxidation and/or nitridation layer is substantially removed from said surface.

In some embodiments, the step of treating said composition under reduced pressure or inert gas comprises treating said composition under reduced pressure or in an inert gas environment at a temperature of 700° C. or greater for at least 10 minutes.

In some embodiments, the step of treating said composition under vacuum or reduced pressure or in an inert gas environment is performed for between 15 minutes to 30 hours.

In some embodiments, the composition comprises zirconium or a zirconium alloy.

In some embodiments, the composition comprises an oxidation layer and the oxidation layer is a blue or blue-black oxidized zirconium.

In some embodiments, the composition further comprises an alloying element selected from the group consisting of titanium, tantalum, hafnium, niobium, and any combination thereof.

In some embodiments, the composition is a composition comprising an alloy of zirconium and niobium, said alloy having a niobium content of at least 1% (w/w).

In some embodiments, the composition is a composition comprising an alloy of zirconium and niobium, said alloy having a niobium content of at least 10% (w/w).

In some embodiments, the composition is a composition comprising an alloy of zirconium, titanium, and niobium, said alloy having a niobium content of at least 10% (w/w).

In some embodiments, the method of reworking the composition further comprises the step of reforming an oxidation and/or nitridation layer on the surface of the substrate after said step of treating.

In some embodiments, the composition forms at least a portion of a workpiece.

In some embodiments wherein the composition forms at least a part of a workpiece, the workpiece is a medical implant, and the method comprises the steps of: treating all or at least a portion of said medical implant under reduced pressure or in an inert gas environment at a temperature of 500° C. or greater until said oxidation and/or nitridation layer is substantially removed from said surface; and, finishing the treated medical implant.

In some embodiments of the method of reworking a medical implant, the method further comprises the step of finishing said medical implant is selected from the group consisting of mass finishing, laser marking, sterilization, and any combination thereof.

In some embodiments of the method of reworking a medical implant, the step of treating all or at least a portion of said medical implant under reduced pressure or inert gas comprises treating said medical implant under reduced pressure or in an inert gas environment at a temperature of 700° C. or greater for at least 10 minutes.

In some embodiments of the method of reworking a medical implant, the step of treating under reduced pressure or in an inert gas environment is performed for between 15 minutes to 30 hours.

In some embodiments of the method of reworking a medical implant, the composition comprises zirconium or a zirconium alloy.

In some embodiments where the composition forms at least a portion of a workpiece and the workpiece is a medical implant, the composition comprises an oxidation layer on said surface and said oxidation layer is a blue or blue-black oxidized zirconium.

In some embodiments where the composition forms at least a portion of a workpiece and the workpiece is a medical implant, the composition comprises zirconium alloy and said zirconium alloy comprises an alloying element selected from the group consisting of titanium, tantalum, hafnium, niobium, and any combination thereof.

In some embodiments where the composition forms at least a portion of a workpiece and the workpiece is a medical implant, the composition comprises an alloy of zirconium and niobium, said alloy having a niobium content of at least 1% (w/w).

In some embodiments where the composition forms at least a portion of a workpiece and the workpiece is a medical implant, the composition comprises an alloy of zirconium and niobium, said alloy having a niobium content of at least 10% (w/w).

In some embodiments where the composition forms at least a portion of a workpiece and the workpiece is a medical implant, the composition comprises an alloy of zirconium, titanium, and niobium, said alloy having a niobium content of at least 10% (w/w).

In some embodiments of the method of reworking a medical implant, the medical implant is selected from the group consisting of a hip implant, a knee implant, a dental implant, a vertebral implant, a shoulder implant, an ankle implant, an elbow implant, and a temporo-mandibular implant.

In some embodiments of the method of reworking a medical implant, the step of treating said composition under reduced pressure or in an inert gas environment is performed for between 10 minutes and 30 hours.

In some embodiments of the method of reworking a medical implant, the method further comprises the step of reforming an oxidation and/or nitridation layer on the surface of the substrate after said step of treating.

Further features, aspects, and advantages of the present invention, as well as the structure and operation of various embodiments of the present invention, are described in detail below with reference to the accompanying drawings.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

Figure 1:
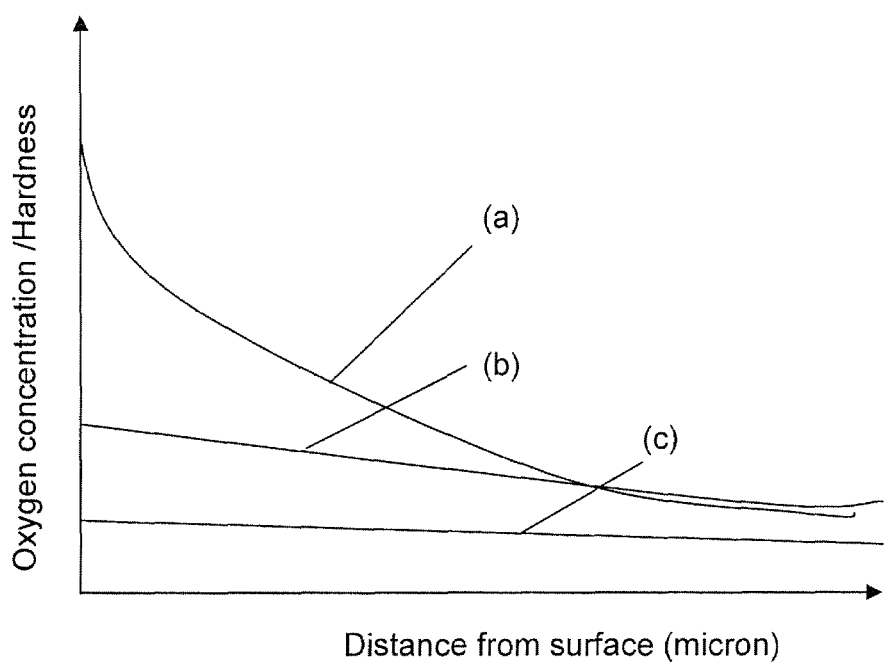
FIG. 1 illustrates two preferred oxygen profiles for re-oxidation (curves (a) and (b)); and one less-than-optimal oxygen profile for re-oxidation (curve (c)).

As used herein, "a" or "an" means one or more. Unless otherwise indicated, the singular contains the plural and the plural contains the singular.

As used herein, "inert gas" is defined as a gas which does not substantially react with the substrate materials described herein. Oxygen and nitrogen, among other gases, are not inert gases under this definition.

The instant invention relates to surface oxidized and/or nitrided compositions that are rejected for non-conformance to specification. Such components have found extensive application in the field of medical implants and the present invention is expected to be particularly usefully applied in this field. After the oxidation and/or nitridation process, rejected workpieces comprising the compositions are typically scrapped because the oxide and/or nitride does not allow for ease of rework. The objective of this invention is to completely dissolve the surface oxide and/or nitride and drive the resultant oxygen or nitrogen homogeneously throughout the composition. Therefore, the workpiece comprising the compositions can be re-oxidized and/or re-nitrided. In the case of the use of the compositions for medical implants, the reworked workpiece and be re-formed (re-oxidized/re-nitrided) into a medical implant.

In general terms, the instant invention relates to the reworking of a composition comprising a substrate and an oxidation and/or nitridation layer on the surface of the substrate. In some embodiments, the composition forms a portion of, or the entirety of, a workpiece. In some embodiments, the workpiece is an orthopaedic implant, such as, but not limited to hip implant, a knee implant, a dental implant, a vertebral implant, a shoulder implant, an ankle implant, an elbow implant, and a temporo-mandibular implant. In this way, the term medical implant includes dental implants.

While most of the remaining discussion focuses on the application of the instant invention where the substrate is zirconium or zirconium alloy and the surface comprises oxidized zirconium such as that described in U.S. Pat. No. 2,987,352 to Watson and U.S. patent U.S. Pat. No. 5,037,438 to Davidson, among others, it should be understood that the instant invention is broader in scope and can be applied to any composition comprising a metallic substrate and an oxidized and/or nitrided surface. Presently, the manufacturing yield of oxidized zirconium components is typically less than 95%. The components that are rejected after the oxidation treatment cannot be reworked due to the oxide on the surface. The removal of oxide with machining or grinding leads to the embedding of the oxide particles on the surface and such components having embedded oxide particles can not be re-oxidized. The general approach had been to scrap these components entirely which leads to reduced output of the product line and increased cost of the final products.

The re-work process involves treating the oxidized zirconium components in vacuum (less than $10^{-2}$ torr) or in reduced pressure (less than about 10 torr) at elevated temperatures (preferably greater than 500° C.) for extended periods. The time, temperature and pressure can be decided based on the starting oxide thickness. Diffusion of oxygen through the entire cross-section will increase the oxygen concentration of the alloy marginally, still keeping it in specification.

In the present method, a vacuum process is used to dissolve the surface oxide and/or nitride. The vacuum or inert gas heat treatment is applied in such a way as to dissolve/diffuse the oxygen and or nitrogen substantially homogeneously throughout the entire substrate until the oxide and/or nitride is substantially completely removed from the surface. For best results, the oxide is preferably completely dissolved such that the oxygen concentration is uniform or near-uniform through the entire substrate. FIG. 1 shows two preferred oxygen profiles for re-oxidation (curves (b) and (c)); and one less-than-optimal oxygen profile for re-oxidation (curve (a)). In one aspect of invention the surface hardness of the alloy prior to re-oxidation is kept below 4.5 GPa. Although the bulk substrate has slightly more oxygen and/or nitrogen as a result of the dissolution/diffusion, the net change in composition is negligible with respect to successive oxidation/nitridation steps.

Broadly, the oxidized and/or nitrided composition is placed in an elevated temperature environment and in a vacuum or a reduced pressure environment (typically less than about $10^{-2}$ torr, although the pressure may be higher if a longer treatment time is used). Alternatively, the oxidized and/or nitrided composition is placed in an inert gas environment in an elevated temperature environment. The treatment under reduced pressure/vacuum environment or under inert gas at elevated temperatures dissolves the oxide and/or nitride. Preferably, the temperature is about 650° C.

Figure 2:
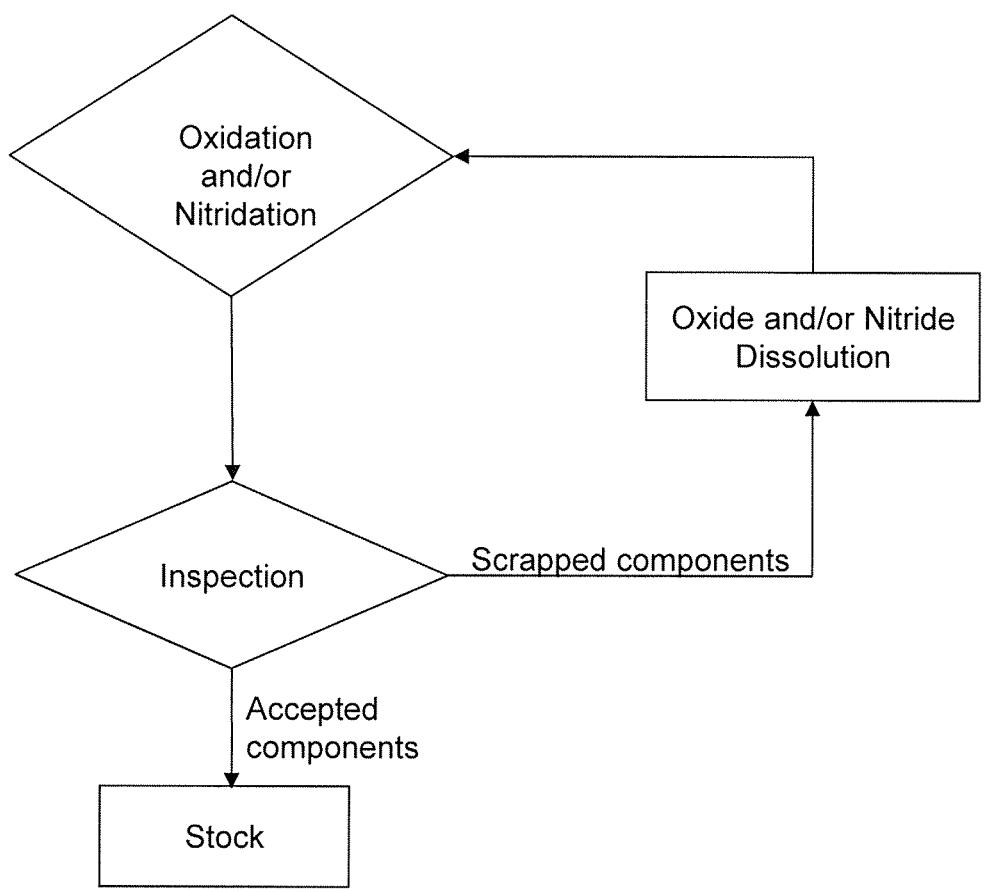
FIG. 2 is a block diagram illustrating the steps in the reworking of surface oxidized composition.

Thus, in the manufacture of an oxidized and/or nitrided composition, components that would otherwise be scrapped are reworked following dissolution of the oxide/nitride. A schematic flow diagram of the manufacturing process incorporating this rework procedure is provided in FIG. 2. The process is identical in the case of nitrided compositions or for mixed oxidized/nitrided compositions.

However, by application of elevated temperature and substantially depriving the composition of oxygen or nitrogen and other non-inert gases causes any surface oxides or nitrides to be dissolved and diffused into the bulk substrate. One means to substantially depriving the composition of oxygen or nitrogen is to treat the composition in a low pressure or vacuum environment (typical $10^{-2}$ torr or less). At such low pressures, concentrations of oxygen and nitrogen as sufficiently low as to preclude further oxide and/or nitride growth as the oxide and/or nitride is dissolved/diffused from the surface into the bulk substrate.

The general method to dissolve the surface oxide and/or nitride from the surface and dissolve the oxygen and/or nitrogen into the bulk substrate comprises the oxidized and/or nitrided composition under reduced pressure or vacuum, or under inert gas the above said implant at a temperature of about 500° C. or greater. The exact temperature is chosen will depend upon the time of treatment and the thickness of the surface layer to be removed. Use of low temperatures will generally require longer treatment times. A thicker surface layer will also require longer treatment times which may be made shorter through the use of higher dissolution/diffusion temperatures. In the case of an oxide, the oxygen atoms thus released are driven deeper into the alloy substrate, hardening the material. The time required is deduced from the diffusion coefficient and desired hardened depth. The approximate relationship is $x^2=D't$, where x is diffusion layer thickness, t is time and D' is an effective diffusion coefficient.

Preferably, the dissolution/diffusion treatment should be performed at the lowest temperature which is feasible under the conditions of oxide thickness and the required time for completion. In this way, a more complete preservation of the microstructure of the substrate is promoted. The oxide is completely dissolved until the oxygen concentration is near uniform through the entire substrate. Preferably, surface hardness of the alloy after re-work and before re-oxidation/re-nitridation is kept below 4.5 GPa.

It should be understood that although the preferred temperature is about 500° C. or greater, the temperature used can be varied, particularly in the case of different substrate compositions. As indicated, it is preferable for optimal results to perform the treatment at the lowest practical temperature.

The re-oxidized compositions can then be used as stock in a finished product manufacturing process. As oxidized and nitrided surfaces have shown particular applicability in the field of medical implants, the present invention is expected to be particularly useful in the manufacture of medical implants. Such medical implants are formed using the reworked composition as stock. Forming the medical implant using the reworked composition as stock may be performed by any suitable method, including those known or obvious to those of ordinary skill in the art.

The present invention is applicable to all oxidized and nitrided surfaces. It is particularly useful in oxidized or nitrided zirconium or zirconium alloy surfaces. It is, for example, applicable to the oxidized zirconium surfaces of Davidson as described in U.S. Pat. Nos. 5,037,438 and 5,180,394, those of Watson as described in U.S. Pat. No. 2,987,352, those of Hunter et al. in U.S. Pat. Nos. 6,447,550; 6,585,7723, and also to a new composition of oxidized zirconium described in copending U.S. utility application Ser. No. 11/558,756 filed Nov. 10, 2006 and corresponding international patent application PCT/US2006/043838 filed Nov. 10, 2006. The foregoing is a list of non-limiting examples, as the present invention is applicable to reworking of all oxidized and nitrided surfaces.

In the case of medical implants having oxidized and/or nitrided surfaces, in some embodiments, the present invention is useful in reclaiming out-of-specification samples. In practice, a medical implant is formed from a metal or metal alloy stock and is then oxidized and/or nitrided to form an oxidized and/or nitrided medical implant. The medical implant may (or may not) be then subjected to various finishing steps. At this point, the implant is tested for conformance to manufacturing specifications. One such specification is the oxide thickness. If the oxide thickness of the implant is less than the specification, such implant will not be accepted. If the oxide thickness is greater than specification, then also the component will not be accepted. Historically, if such implants were deemed to be outside of specifications, it would be discarded as scrap. In one embodiment of the present invention, the medical implant, or a portion thereof, is treated according to the present invention such that the oxidized and/or nitrided surface is dissolved to rework the implant and the implant can thereafter be either re-oxidized and/or re-nitrided, or otherwise finished into a useful medical implant. Finishing steps include, but are not limited to mass-finishing to obtain a desired final finish, laser marking to identify the implant and packaging, sterilization of the implant as a final step, etc. The mass-finish can typically be employed using abrasive media. The other techniques of polishing such as that using diamond media may also be employed. Sterilization may be carried out using gamma rays, or other methods found in the art.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of reworking a substrate, said method comprising the steps of providing a substrate comprising zirconium or a zirconium alloy, said substrate having a first layer on its surface comprising at least one of an oxide and a nitride formed at least by exposing said substrate to ceramic-forming species in an environment having a temperature of at least 500 degrees C.;

treating said substrate under vacuum or in an inert gas environment at a temperature of 500 degrees C. or greater until said oxide and/or nitride in said first layer is substantially removed from said surface; and reforming a second layer on the entire surface of the substrate after said step of treating, said second layer comprising at least one of an oxidation layer, a nitridation layer and an oxidation and nitridation layer.

2. The method of claim 1, wherein said step of treating said substrate under vacuum or inert gas comprises treating said substrate under vacuum or in an inert gas environment at a temperature of 700 degrees C. or greater for at least 10 minutes.

3. The method of claim 1, wherein said step of treating said substrate under vacuum or in an inert gas environment is performed for between 15 minutes to 30 hours.

4. The method of claim 1, wherein said first layer comprises a blue or blue-black oxidized zirconium.

5. The method of claim 1, wherein said substrate further comprises an alloying element selected from the group consisting of titanium, tantalum, hafnium, niobium, and any combination thereof.

6. The method of claim 5, wherein said substrate comprises an alloy of zirconium and niobium, said alloy having a niobium content of at least 1% (w/w).

7. The method of claim 5, wherein said substrate comprises an alloy of zirconium and niobium, said alloy having a niobium content of at least 10% (w/w).

8. The method of claim 5, wherein said substrate comprises an alloy of zirconium, titanium, and niobium, said alloy having a niobium content of at least 10% (w/w).

9. The method of claim 1, wherein said substrate forms at least a portion of a workpiece.

10. The method of claim 1 wherein said treating step provides said substrate with a hardness level of below 4.5 GPa after substantial removal of said oxide and/or nitride in said first layer.

11. The method of claim 1 wherein said treating step comprises treating said substrate under vacuum or in an inert gas environment at a temperature in the range of 500 degrees C. to 650 degrees C. for at least 10 minutes.

12. The method of claim 1 where said first layer comprises an oxide and said second layer comprises a nitridation layer.

13. A method of reworking a medical implant, said method comprising the steps of:

providing a medical implant, at least a portion of said medical implant comprising a substrate having a first layer on its surface comprising at least one of an oxide and a nitride formed at least by exposing said substrate to ceramic-forming species in an environment having a temperature of at least 500 degrees C., treating said substrate under vacuum or in an inert gas environment at a temperature of 500 degrees C. or greater until said oxide and/or nitride in said first layer is substantially removed from said surface;

wherein the volume of said substrate is sufficient to allow said substrate to have an oxygen and/or nitrogen concentration that remains within specification after said treating step and corresponding removal of said oxide and/or nitride;

reforming a second layer on the entire surface of said substrate, said second layer comprising at least one of an oxidation layer, a nitridation layer and an oxidation and nitridation layer and, finishing the treated medical implant.

14. The method of claim 13, wherein the step of finishing said medical implant is selected from the group consisting of mass finishing, laser marking, sterilization, and any combination thereof.

15. The method of claim 13, wherein said step of treating said substrate under vacuum or inert gas comprises treating said medical implant under vacuum or in an inert gas environment at a temperature of 700 degrees C. or greater for at least 10 minutes.

16. The method of claim 13, wherein said step of treating under vacuum or in an inert gas environment is performed for between 15 minutes to 30 hours.

17. The method of claim 13, wherein said medical implant comprises zirconium or a zirconium alloy.

18. The method of claim 17, wherein said first layer comprises a blue or blue-black oxidized zirconium.

19. The method of claim 17, wherein said medical implant comprises zirconium alloy and said zirconium alloy comprises an alloying element selected from the group consisting of titanium, tantalum, hafnium, niobium, and any combination thereof.

20. The method of claim 19, wherein said medical implant comprises an alloy of zirconium and niobium, said alloy having a niobium content of at least 1% (w/w).

21. The method of claim 19, wherein said medical implant comprises an alloy of zirconium and niobium, said alloy having a niobium content of at least 10% (w/w).

22. The method of claim 19, wherein said medical implant comprises an alloy of zirconium, titanium, and niobium, said alloy having a niobium content of at least 10% (w/w).

23. The method of claim 13, wherein said medical implant is selected from the group consisting of a hip implant, a knee implant, a dental implant, a vertebral implant, a shoulder implant, an ankle implant, an elbow implant, and a temporomandibular implant.

24. The method of claim 13, wherein said step of treating said substrate under vacuum or in an inert gas environment is performed for between 10 minutes and 30 hours.

25. A method of reworking a substrate, said method comprising the steps of providing a substrate comprising a first layer on its surface, said first layer comprising at least one of an oxide and a nitride formed at least by exposing said substrate to ceramic-forming species in an environment having a temperature of at least 500 degrees C., treating said substrate under vacuum or in an inert gas environment at a temperature of 500 degrees C. or greater until said oxide and/or nitride in said first layer is substantially removed from said surface;

wherein the volume of said substrate is sufficient to allow said substrate to have an oxygen and/or nitrogen concentration that remains substantially the same after said treating step and corresponding removal of said oxide and/or nitride; and reforming a second layer on the entire surface of said substrate after said step of treating, said second layer comprising at least one of an oxidation layer, a nitridation layer and an oxidation and nitridation layer;

wherein said substrate comprises zirconium or a zirconium alloy.

26. The method of claim 25 wherein said vacuum environment is $10^{-2}$ torr or less to substantially deprive said substrate of oxygen or nitrogen.

* * * * *